United States Patent [19]
Godfrey

[11] Patent Number: 5,968,536
[45] Date of Patent: *Oct. 19, 1999

[54] DEVICE FOR APPLYING TOPICAL ANESTHETIC

[76] Inventor: Marjorie M. Godfrey, 53 Dartmouth Ave., Lebanon, N.H. 03766

[*] Notice: This patent issued on a continued prosecution application filed under 37 CFR 1.53(d), and is subject to the twenty year patent term provisions of 35 U.S.C. 154(a)(2).

[21] Appl. No.: 08/540,642

[22] Filed: Oct. 11, 1995

[51] Int. Cl.$^6$ .............................. A61F 13/00; A61K 9/70
[52] U.S. Cl. ..................... 424/402; 424/443; 424/445; 424/447
[58] Field of Search .................................. 424/402, 443, 424/446, 447, 445; 604/305, 308; 514/817

[56] References Cited

U.S. PATENT DOCUMENTS 5,041,287   8/1991   Driggers et al. ........................... 424/47

OTHER PUBLICATIONS

Selby, I.R., "Analgesia for Venous Cannulation", Journal of the Royal Society of Medicine, vol. 88, pp. 264–267, May 1995.
Chang, et al., A Multicentre Randomized Study of Single–Unit Dose Package, Canadian Journal of Anaesthesia, vol. 41(1), pp. 59–63, 1994.
Norman, et al., "Complications of the Use of EMLA," British Journal of Anaesthesia, vol. 64, pp. 403–406, 1990.
Robieux, et al., "Pain Perception and Effectiveness of the Eutectic," International Pediatric Research Foundation., Inc., vol. 32, No. 5, 1992.
Buckley, et al., "Eutectic Lidocaine/Prilocaine Cream," Drug Evaluation, vol. 46 (1), pp. 126–151, 1993.
Gajraj, et al., "Eutectic Mixture of Local Anesthetics," Anesthesia Analg, vol. 78, pp. 574–583, 1994.
Sims, "Thickly and Thinly Applied Ligocaine–Prilocaine Cream," Anesthesia and Intensive Care, vol. 19, No. 3, Aug. 1991.
Zappa, "Another Advantage of EMLA Cream," Pediatric Nursing, vol. 20, No. 4, Aug. 1994.
Wolf, et al., EMLA Cream for Painless Skin Testing,: Annals of allergy, vol. 73, Jul. 1994.
Nilsson, et al., "The EMLA Patch," Anaesthesia, vol. 49, pp. 70–72, 1994.
Lurngnateetape, et al., "Placebo Effect of Eutectic Mixture of Lidocaine and Prilocaine," Annals Academy of Medicine, vol. 23, No. 4, Jul. 1994.
Arts, et al., "Age–Related Response to Lidocaine–Prilocaine," Pediatrics, vol. 93, No. 5, May 1994.
Sakamoto, et al., "Dermal Patch Anaesthesia," Anaesthesia, vol. 48, pp. 390–392, 1993.

*Primary Examiner*—Raj Bawa
*Attorney, Agent, or Firm*—Hale and Dorr LLP

[57] ABSTRACT

A device for applying a topical anesthetic includes a body to be wrapped around a part of the patient to provide a conformed fit. When wrapped, the body has an inside surface facing the part where a holder for holding a topical anesthetic against the patient's skin is provided and covered with a removable seal. The device can take a number of forms, such as a glove, a sock, or a tube. When wrapped, the device provides a comfortable and snug fit. The device has integral hook and loop regions for easy attachment and removal.

21 Claims, 4 Drawing Sheets

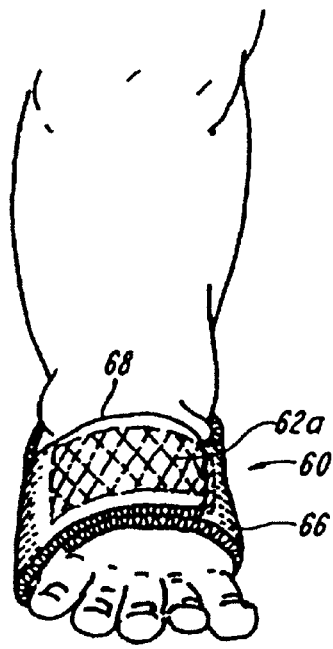
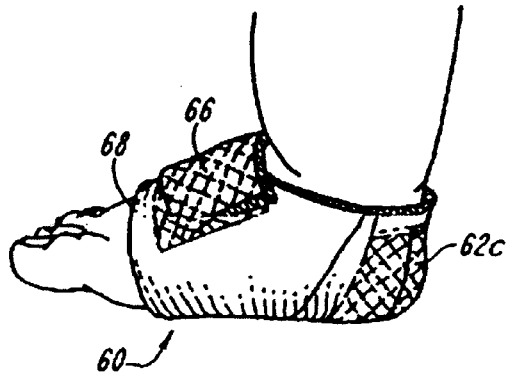
FIG. 3A  FIG. 3B
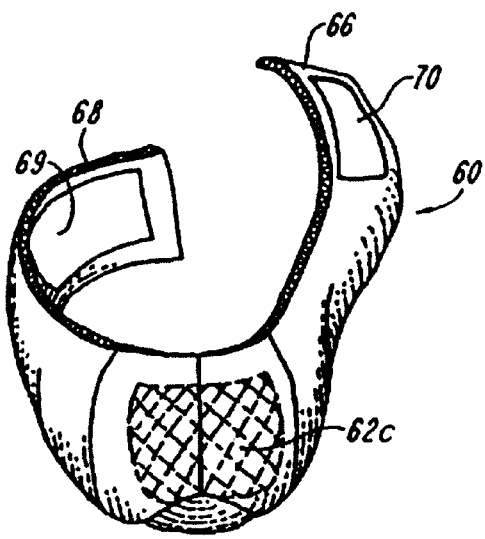
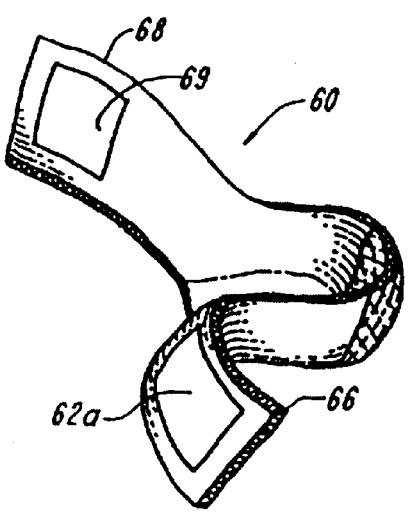
FIG. 3C  FIG. 3D

DEVICE FOR APPLYING TOPICAL ANESTHETIC

BACKGROUND OF THE INVENTION

Medical practitioners insert intravenous (IV) catheters through a patient's skin to provide access for medications, fluids, and blood drawing. Insertion of an IV catheter can cause pain, which can reduce the level of cooperation by the patient, and can cause anxiety and other negative effects on the physical and mental well-being of the patient. The problems are particularly acute when the patient is a child.

To prepare the patient's skin for inserting a catheter, a practitioner cleans the skin and then anesthetizes it to reduce the pain. A topical anesthetic with 40% lidocaine has been used, but its use has been inconsistent because of concerns about irritation to the skin, systemic toxicity, and inadequate analgesia. Lidocaine-based anesthetics have also been injected, but this method of anesthetizing requires a needle stick. Attempts have been made, therefore, to produce a more desirable local anesthetic for IV insertions.

A promising topical anesthetic is sold under the name EMLA® (a registered trademark, and an acronym for "eutectic mixture of local anesthetics"). This anesthetic, which is typically applied as a cream, produces anesthesia equivalent to that achieved with a lidocaine injection, but without the needle stick. Even though EMLA anesthetic has been approved by the FDA, it is used to varying degrees because of difficulties in its application and use, and resulting non-compliance by patients.

To apply this anesthetic, a practitioner applies about 1–2 grams of cream per 10 $cm^2$ of skin and leaves it on the skin for about an hour. An adhesive dressing, such as a TEGADERM® dressing (a registered trademark of 3M, located in St. Paul, Minn.), is often used to cover the cream and to keep it in contact with the skin. This dressing can be difficult to apply, however, and has some documented risks. The dressing has an adhesive that has a tendency to stick to itself, making it difficult to apply to skin surfaces. Moreover, it can lose its adhesion if the adhesive comes into contact with the cream. Secondary dressings, such as household plastic wrap and gauze, have been used to compensate for these problems.

Several other problems, particularly involving children, have been reported when applying the anesthetic in this manner. Children have rubbed the cream into their eyes when an inadequate covering has been applied to the hands, have ingested the cream and therefore caused upper airway anesthesia, and have chewed on the dressing.

Another way to apply this anesthetic has been with a patch impregnated with the anesthetic. To apply the patch, a seal is peeled away, so that the anesthetic can contact the patient's skin, and so that a stiff foam tape around the anesthetic holds the patch on the patient. This tape can become loose with flexion and movement, however, causing it to lose its adhesion, and thereby raising the risks to children as noted above. Patients may also have sensitivity to the tape on the patch and to its painful removal.

It is therefore an object of the present invention to improve the application of a topical anesthetic for injections, while reducing the drawbacks and risks that have been associated with the application of anesthetics.

SUMMARY OF THE INVENTION

The present invention includes a device and method that improve the application of a topical anesthetic and reduce the drawbacks of prior devices and methods by using a body that is wrapped around a part of the patient to provide a flexible comfortable fit. The body can be provided in one of a number of different forms, including a glove, a sock, or a tube, and should easily conform to the body part about which it is wrapped. When wrapped, the body has an inside surface that faces the part of the patient to be anesthetized.

A medication holder for holding a topical anesthetic against the patient's skin is provided on the inside surface of the body. The holder preferably includes a cloth material impregnated with anesthetic and covered with an easily removable seal; alternatively, the holder could be a shallow well for holding cream.

The body has an easily attachable and removable closure means, such as a hook and loop system, straps, clips, or other means. Accordingly, the body, medication holder, and closure means are preferably provided as a single unit, making it easy to apply the anesthetic with the device. Preferably, no adhesive is required or used to hold the anesthetic against the patient because an adhesive can lose its adhesion; rather, the primary means for holding the device against the patient is with the flexible material and the closure means.

The device of the present invention assists in the secure, safe, and easy application of topical anesthetic, and thus helps to reduce instruction time, decrease risks to children, and increase the likelihood of success of the anesthetic. The device can therefore reduce or eliminate pain and stress for a variety of procedures, including venipuncture, radial artery cannulation, lumbar punctures, blood drawings, cannulation for hemodialysis, bone marrow aspirations, vaccinations, fingersticks for blood draws, subcutaneous injections, and injections in subcutaneous reservoirs in children with cancer. Moreover, with the easy and comfortable application of a topical anesthetic, more procedures can be performed on an outpatient basis, thus decreasing medical costs. Other features and advantages will become apparent from the following detailed description, drawings and claims.

BRIEF DESCRIPTION OF THE DRAWINGS

FIGS. 2(a)–2(b), 3(a)–3(d), and 4(a)–4(c) are perspective views of a glove system, a sock system, and a tube system, respectively, according to the present invention.

DETAILED DESCRIPTION

Several different types of devices are provided for applying a topical anesthetic, such as an eutectic mixture of local anesthetics (emla). The devices work in a generally similar manner, and preferably have a number of common features and benefits. It is particularly desirable for the device to have a body with a medication holder and closure means so that the device is easy to position, wrap, secure, and remove; is comfortable when worn; and does not have a significant likelihood of leakage from the area of the patient that is to be anesthetized.

Figure 1A:
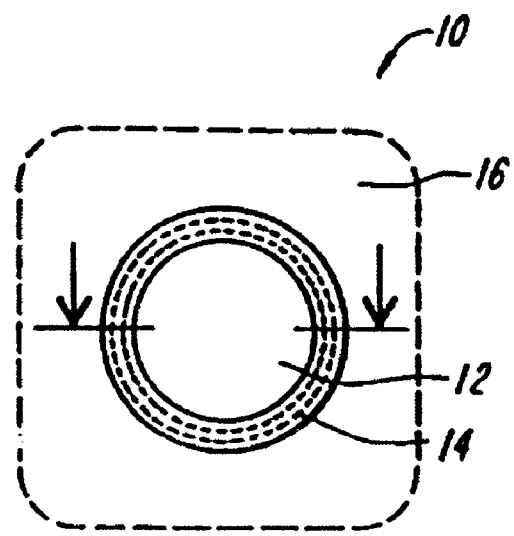
FIGS. 1(a) and 1(b) are a plan view and a cross-sectional view, respectively, of a medication holder with a patch for holding a topical anesthetic.
Figure 1B:
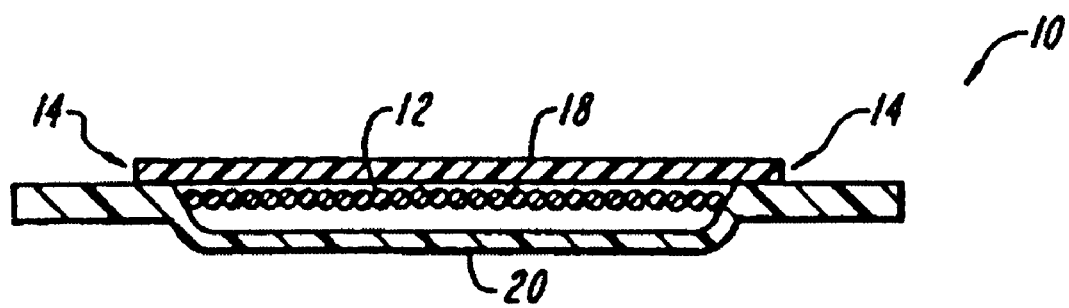

Referring to FIGS. 1(a) and 1(b), a medication holder 10 can take the form of a patch and can have a size and shape that can be modified to fit in different types of devices for different parts of the body. Holder 10 includes a cloth or cloth-like disk 12 that is saturated with anesthetic, preferably 1 g of a eutectic mixture in a 5% emulsion. Disk 12 is mounted against a backing laminate 18, and is surrounded with an annular seal area 14. In a prior known patch, an adhesive area 16 (shown in dashed line) would surround seal area 14. Such an adhesive area is preferably omitted according to the present invention, because adhesives can lose adhesion through contact with cream, or due to flexion. A closure laminate 20 covers disk 12, and can easily be peeled off seal area 14 to expose the anesthetic impregnated in disk 12.

Figure 2A:
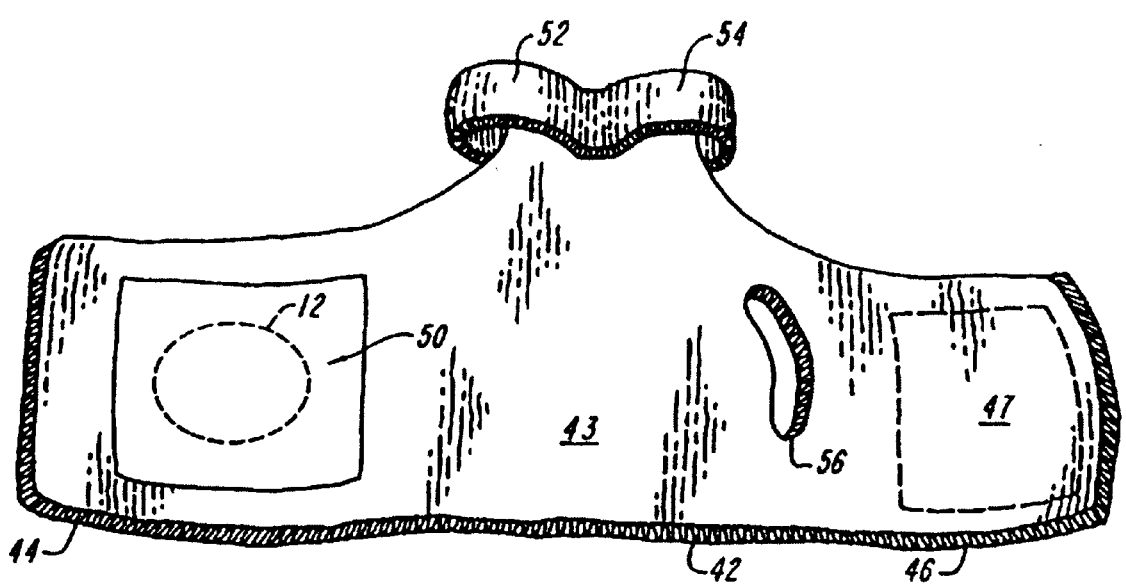
Figure 2B:
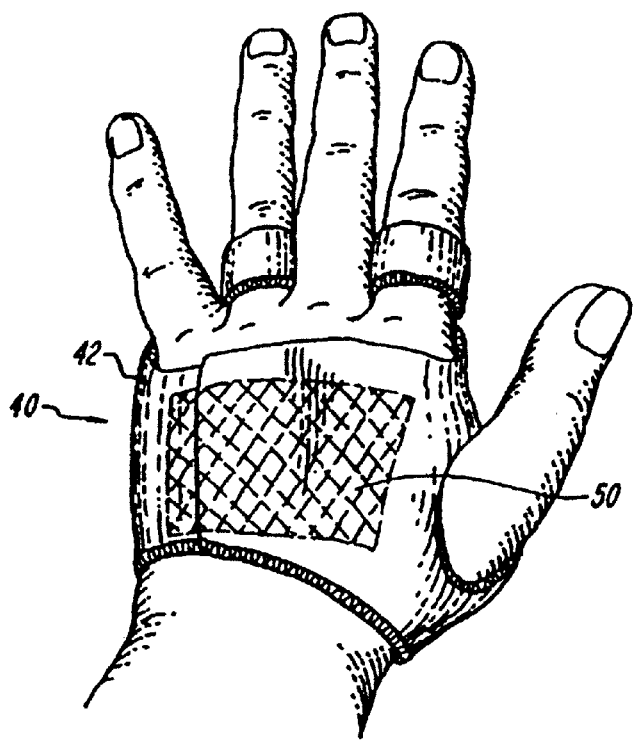

Referring to FIGS. 2(a) and 2(b), a device for applying anesthetic to a patient's hand takes the form of a fingerless glove 40 when worn. Glove 40 has a body 42 made of a comfortable, flexible material that conforms to the contours and texture of the skin, and that tolerates movement and flexion. An exemplary material is a synthetic rubber, such as a product known as NEOPRENE®. Other materials that conform to the shape of a hand, flex freely, and tolerate movement while maintaining contact with the skin surface, can be used, such as latex or a cotton/lyrca/spandex material. If latex is used, other options should be available because some people are sensitive to latex. It is also desirable, particularly when the patients are children, that the material be provided in colorful and attractive designs so that children will be more likely to want to wear such a glove.

In an open position as shown in FIG. 2(a), body 42 is generally planar and includes a central palm portion 43 and integral flaps 44, 46 at opposite ends of the palm portion 43. Flaps 44, 46 have an integral closure means, which is preferably provided as hook and loop regions, such as those used in a VELCRO® hook and loop fastener. Flap 44 has a region on an outside surface (not shown) with hooks, while flap 46 has an inside surface (i.e., a surface that faces the patient when the glove is worn) with a region 47 of loops. Alternatively, the hooks and loops can be on flaps 46 and 44, respectively.

Flap 44 has on its inside surface a medication holder 50 that holds the anesthetic, preferably with a disk impregnated with a topical anesthetic as described in conjunction with FIGS. 1(a) and 1(b). In this case, the backing laminate 18 (FIG. 1(b)) is attached to the body.

As shown in FIG. 2(a), the glove is open and is not "glove-shaped" before it is placed on the hand; otherwise, the anesthetic could smear if the glove had to be pulled over the hand. The open design avoids smearing and also helps provide accurate placement of medication holder 50.

To fit the glove, an appropriately sized glove is selected, and a closure laminate 20 is peeled off to expose the anesthetic (FIG. 1). The patient inserts his or her fingers and thumb into a ring finger loop 52, an index finger loop 54, and a thumb opening 56, so that the palm of the patient's hand faces palm portion 43. Loops 52, 54 and opening 56 help position the glove and keep it in position when closed. Flap 44 is folded over the back of the hand so that the anesthetic in well 50 contacts the hand at a desired location on the back of the hand. Flap 46 is then folded over flap 44 so that the loops in region 47 contact the hooks in the region on the outside surface of flap 44. If properly fitted, the glove should now hold securely and conform to the shape of the hand such that normal hand flexion and other movement should not allow any anesthetic to escape from the area that is being anesthetized. The glove is preferably positioned and worn without an adhesive, which could otherwise become loosened from flexion.

After the glove has been left in place for a desired time, typically about sixty minutes, a catheter or needle can be inserted. To remove the glove, the hooks and loops are easily pulled apart and flaps 44, 46 are opened to expose the anesthetized site. Thus, the closure means can be opened with a single motion from one hand, allowing the patient to remove the glove when enough time has lapsed, or in case of discomfort.

Referring to FIGS. 3(a)–3(d), to provide anesthetic to the top or heel of the foot (as is sometimes done with infants), a device is provided in the form of a sock 60. A closure means and a medication well are generally similar to those in glove 40. As with the glove, the sock shape is not evident when in the open position, but the sock is wrapped around the foot to accurately place the medication holder and to avoid smearing of the anesthetic.

A medication holder 62a, 62c can be located on top of the foot, as shown in FIGS. 3(a) and 3(d), or on the heel, as shown in FIGS. 3(b) and 3(c), or both. A closure laminate over holder 62a, 62c is removed and the sock is placed on the foot. When the holder is to be placed over the heel, it is positioned over the site to be anesthetized when the sock is positioned; when the holder is to be placed over the top of the foot, the holder is on a flap 66. After flap 66 is positioned, a flap 68 is crossed over the top of the flap 66 to close the sock with hook and loop regions located on flaps 66, 68. A loop region 69 is shown on flap 68 in FIGS. 3(c) and 3(d), while a hook region 70 is shown on flap 66 in FIG. 3(c).

As is done with the glove, the sock is kept on for a desired time, and then it is removed by pulling apart the hook and loop regions with one easy motion.

Figure 4A:
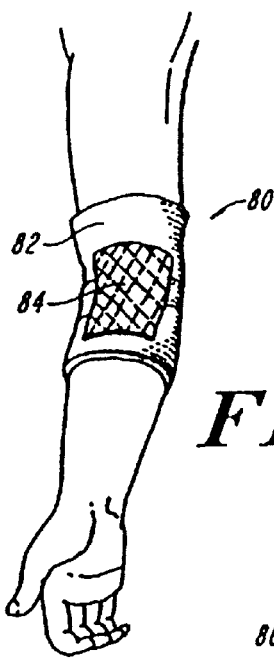
Figure 4B:
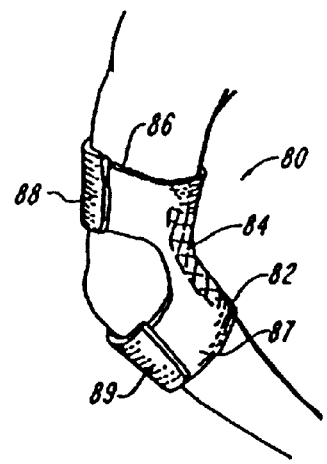
Figure 4C:
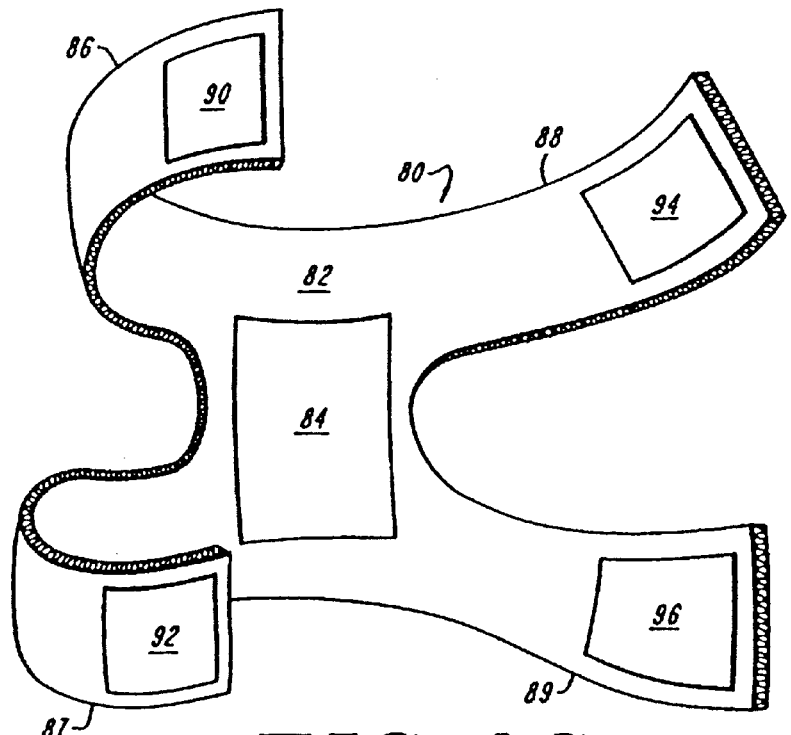

Referring to FIGS. 4(a) and 4(b), a device is provided in the form of a tube 80 to apply a topical anesthetic to a patient's antecubital region. Tube 80 has a central body 82, a medication holder 84 on the inside surface of body 82, and flaps 86, 87, 88, and 89. Hook regions 90, 92 are on flaps 85, 87 and loop regions 94, 96 are on flaps 88, 89.

To use the tube system, an appropriately sized tube is chosen, a closure laminate over a medication holder is removed, and the medication holder with anesthetic is positioned over the insertion site. Flaps 86, 87 are positioned over the arm, and flaps 88, 89 are crossed over to close the tube. Unlike the sock and the glove, the medication holder for tube 80 is on the main body instead of on one of the flaps.

The patch that is provided on the body of the device can be designed for one-time usage, or the holder may include slots or some other mechanism to allow patches to be replaceably and reusably provided on the body before the body is wrapped around a body part of the patient.

Figure 5:
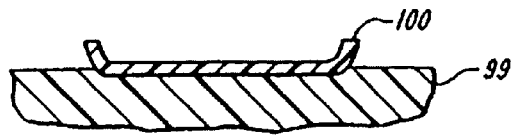
FIG. 5 is a cross-sectional view of a medication holder that includes a shallow well on a flexible body.

Referring to FIG. 5, as an alternative to a patch, a shallow well 100 for holding an anesthetizing topical cream can be provided against a body 99. This well may be a shallow disk for holding the cream, and can be reusable, assuming the materials allow for appropriate cleansing. The well is preferably designed and made of an appropriate material so that it is durable but also has softness and flexibility at the sides so that it is comfortable when worn.

Having described certain preferred embodiments, it should be apparent that other modifications can be made without departing from the scope of the invention as defined by the appended claims. Hook and loop regions have been described as a preferred closure means, but a different closure means can be used, such as straps for tying, buckles, or clips. Whatever the structure, the closure means should preferably be easy to close and easy to release, preferably with one hand, and more preferably with one motion of one hand. While three particular shapes have been shown and described above, other shapes could be used to anesthetize these or other areas on the body.

What is claimed is:

1. A device providing a topical anesthetic to a body part of a patient, the device comprising:

a flexible, conformable body for wrapping around said body part of the patient and having an inside surface for facing said body part of the patient;

a topical anesthetic; and a patch for holding the topical anesthetic, the patch being mounted to the inside surface of the body so that when the patch is holding the topical anesthetic and the device is wrapped around the patient, the patch with the topical anesthetic contacts the patient, the conformable body holding the patch against the body part of the patient without use of an adhesive between the patient and the body.

2. The device of claim 1, further comprising closure means for closing the body about the body part, said closure means being easily closable and releasable.

3. The device of claim 2, wherein said closure means includes a hook region and a loop region, said hook region and said loop region fastening together when said body is wrapped around the body part.

4. The device of claim 1, wherein said body, when wrapped around a patient's hand, includes a palm portion over the patient's palm, a portion over the back of the patient's hand, and at least one opening for receiving a finger.

5. The device of claim 4, wherein said body further includes two flap portions for crossing over the back of the patient's hand and overlapping each other, the flap portions including closure means for holding the body closed around the patient's hand without an adhesive on the patient's hand.

6. The device of claim 1, wherein said body, when wrapped around a patient's foot, has a heel portion for covering the patient's heel and a portion wrapped around the top and bottom of the patient's foot.

7. The device of claim 6, wherein said body has two flap portions for crossing over the top of the patient's foot and for overlapping each other, the flap portions including closure means for holding the body closed around the patient's foot without an adhesive on the patient's foot.

8. The device of claim 1, wherein said body, when wrapped around a patient's elbow, has a tubular shape.

9. The device of claim 8, wherein said body has a central region for facing an antecubital region and two pairs of flaps for crossing over an arm of the patient above and below the patient's elbow.

10. The device of claim 1, further comprising a manually removable covering over said patch for covering said topical anesthetic prior to use.

11. The device of claim 1, wherein the topical anesthetic includes a eutectic mixture of local anesthetics.

12. The device of claim 10, wherein the covering includes a peelable laminate.

13. A device providing a topical anesthetic to a part of a patient, the device comprising:

a flexible, conformable body for wrapping around the part of the patient to provide a conformed fit, said body including:

a first portion with a surface for facing the part of the patient to be anesthetized, and flap portions integral with the first portion and including closure means for closing the body around and releasing the body from the part of the patient, the closure means holding the body to the part of the patient without the use of an adhesive between the body and the part of the patient; and means, disposed on said surface of said first portion of ssaid flexible body, for holding a topical anesthetic against a part of the patient when the body is wrapped around the part of the patient.

14. The device of claim 13, further comprising a peelable cover over said holding means.

15. The device of claim 13, wherein said topical anesthetic includes a eutectic mixture of local anesthetics.

16. The device of claim 13, wherein said body, when wrapped around a patient's hand, has a palm portion over the patient's palm a portion over the back of the hand and at least one opening for receiving a finger.

17. The device of claim 13, wherein said body, when wrapped around a patient's foot, has a heel portion for covering the heel and a portion wrapped around the top and bottom of the foot.

18. The device of claim 13, wherein said holder includes a well, and wherein said topical anesthetic is in the form of a cream.

19. The device of claim 1, wherein the patch includes a cloth material.

20. The device of claim 13, wherein the holding means includes a patch.

21. The device of claim 13, wherein the holding means includes a well.

* * * * *